(12) United States Patent
Kerr

(10) Patent No.: US 8,469,991 B2
(45) Date of Patent: Jun. 25, 2013

(54) APPARATUS FOR PERFORMING AN ELECTROSURGICAL PROCEDURE

(75) Inventor: Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 459 days.

(21) Appl. No.: 12/792,097

(22) Filed: Jun. 2, 2010

(65) Prior Publication Data
US 2011/0301606 A1    Dec. 8, 2011

(51) Int. Cl.
*A61B 18/14*    (2006.01)

(52) U.S. Cl.
USPC .......................................... 606/205; 606/51

(58) Field of Classification Search
USPC .................... 606/45–52, 205–207
See application file for complete search history.

(56) References Cited

U.S. PATENT DOCUMENTS

| | | | |
|---|---|---|---|
| D263,020 S | 2/1982 | Rau, III | |
| 4,655,215 A | 4/1987 | Pike | |
| D295,893 S | 5/1988 | Sharkany et al. | |
| D295,894 S | 5/1988 | Sharkany et al. | |
| 5,133,727 A * | 7/1992 | Bales et al. | 606/170 |
| 5,209,747 A | 5/1993 | Knoepfler | |
| 5,250,056 A | 10/1993 | Hasson | |
| 5,318,589 A | 6/1994 | Lichtman | |
| D348,930 S | 7/1994 | Olson | |
| 5,352,223 A * | 10/1994 | McBrayer et al. | 606/51 |
| 5,368,600 A | 11/1994 | Failla et al. | |
| 5,403,342 A | 4/1995 | Tovey et al. | |
| 5,454,378 A | 10/1995 | Palmer et al. | |
| 5,471,992 A * | 12/1995 | Banik et al. | 600/564 |
| 5,499,997 A | 3/1996 | Sharpe et al. | |
| 5,509,922 A | 4/1996 | Aranyi et al. | |
| 5,599,350 A | 2/1997 | Schulze et al. | |
| 5,603,723 A | 2/1997 | Aranyi et al. | |
| 5,611,813 A | 3/1997 | Lichtman | |
| 5,620,459 A | 4/1997 | Lichtman | |
| 5,626,609 A | 5/1997 | Zvenyatsky et al. | |
| 5,643,294 A | 7/1997 | Tovey et al. | |
| D384,413 S | 9/1997 | Zlock et al. | |
| 5,697,949 A * | 12/1997 | Giurtino et al. | 606/205 |
| D424,694 S | 5/2000 | Tetzlaff et al. | |
| D425,201 S | 5/2000 | Tetzlaff et al. | |
| 6,106,542 A | 8/2000 | Toybin et al. | |
| 6,270,508 B1 | 8/2001 | Klieman et al. | |
| D449,886 S | 10/2001 | Tetzlaff et al. | |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

International Search Report EP11168419.7 dated Aug. 8 2011.

(Continued)

*Primary Examiner* — Michael Peffley

(57) ABSTRACT

An endoscopic forceps is provided and includes a housing having a shaft that extends therefrom. An end effector assembly is operatively connected to a distal end of the shaft and includes a pair of pivotably coupled first and second jaw members. One of the jaw members is movable relative to the other jaw member. A drive mechanism includes a driving structure in operative communication with a cam slot operably disposed on one of the first and second jaw members. The driving structure includes a detent.

15 Claims, 4 Drawing Sheets

U.S. PATENT DOCUMENTS

| | | | |
|---|---|---|---|
| D457,958 S | 5/2002 | Dycus et al. |
| D457,959 S | 5/2002 | Tetzlaff et al. |
| 6,419,675 B1 | 7/2002 | Gallo, Sr. |
| 6,682,528 B2 | 1/2004 | Frazier et al. |
| 6,743,240 B2 | 6/2004 | Smith et al. |
| D493,888 S | 8/2004 | Reschke |
| D496,997 S | 10/2004 | Dycus et al. |
| D499,181 S | 11/2004 | Dycus et al. |
| D509,297 S | 9/2005 | Wells |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,766,910 B2 | 8/2010 | Hixson et al. |
| 7,887,536 B2 | 2/2011 | Johnson et al. |
| 7,918,848 B2 | 4/2011 | Lau et al. |
| 7,951,150 B2 | 5/2011 | Johnson et al. |
| 8,016,827 B2 | 9/2011 | Chojin |
| 8,112,871 B2 | 2/2012 | Brandt et al. |
| 8,133,254 B2 | 3/2012 | Dumbauld et al. |
| 8,137,273 B2 | 3/2012 | Everett et al. |
| 8,142,473 B2 | 3/2012 | Cunningham |
| 8,162,965 B2 | 4/2012 | Reschke et al. |
| 8,187,273 B2 | 5/2012 | Kerr et al. |
| 8,197,479 B2 | 6/2012 | Olson et al. |
| 8,226,650 B2 | 7/2012 | Kerr |
| 8,251,994 B2 | 8/2012 | McKenna et al. |
| 8,266,783 B2 | 9/2012 | Brandt et al. |
| 8,277,446 B2 | 10/2012 | Heard |
| 8,277,447 B2 | 10/2012 | Garrison et al. |
| 8,282,634 B2 | 10/2012 | Cunningham |
| 8,287,536 B2 | 10/2012 | Mueller et al. |
| 8,292,886 B2 | 10/2012 | Kerr et al. |
| 8,323,310 B2 | 12/2012 | Kingsley |
| 8,343,150 B2 | 1/2013 | Artale |
| 8,343,151 B2 | 1/2013 | Siebrecht et al. |
| 2006/0217697 A1 | 9/2006 | Lau et al. |
| 2007/0173814 A1 | 7/2007 | Hixson et al. |
| 2007/0260242 A1 | 11/2007 | Dycus et al. |
| 2009/0209960 A1 | 8/2009 | Chojin |
| 2010/0023009 A1 | 1/2010 | Moses et al. |
| 2010/0076432 A1 | 3/2010 | Horner |
| 2010/0087816 A1 | 4/2010 | Roy |
| 2010/0094271 A1 | 4/2010 | Ward et al. |
| 2010/0094287 A1 | 4/2010 | Cunningham et al. |
| 2010/0100122 A1 | 4/2010 | Hinton |
| 2010/0130971 A1 | 5/2010 | Baily et al. |
| 2010/0179543 A1 | 7/2010 | Johnson et al. |
| 2010/0179545 A1 | 7/2010 | Twomey et al. |
| 2010/0179546 A1 | 7/2010 | Cunningham |
| 2010/0249769 A1 | 9/2010 | Nau, Jr. et al. |
| 2010/0280511 A1 | 11/2010 | Rachlin et al. |
| 2011/0034918 A1 | 2/2011 | Reschke |
| 2011/0046623 A1 | 2/2011 | Reschke |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1 | 3/2011 | Mueller |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0077648 A1 | 3/2011 | Lee et al. |
| 2011/0082494 A1 | 4/2011 | Kerr et al. |
| 2011/0098689 A1 | 4/2011 | Nau, Jr. et al. |
| 2011/0118736 A1 | 5/2011 | Harper et al. |
| 2011/0184405 A1 | 7/2011 | Mueller |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0238066 A1 | 9/2011 | Olson |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 20121161 | 4/2002 |
| DE | 10045375 | 10/2002 |
| DE | 20 2007 00931 | 10/2007 |
| DE | 19738457 | 1/2009 |
| EP | 0584787 | 3/1994 |
| EP | 1159926 | 12/2001 |
| EP | 1177771 A1 | 2/2002 |
| EP | 1777771 | 2/2002 |
| EP | 1301135 | 9/2005 |
| GB | 2213416 | 8/1989 |
| JP | 617501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1998 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/17448 | 3/2001 |
| WO | WO 01/54604 | 8/2001 |
| WO | WO 2005/110264 | 11/2005 |
| WO | WO2008045348 A2 | 4/2008 |
| WO | WO 2009039179 | 3/2009 |

OTHER PUBLICATIONS

International Search Report EP11168419.7 dated Oct. 11, 2011.
International Search Report EP11168455.1 dated Sep. 26, 2011.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (1965-02-06), British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" . Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; Vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234. No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'L Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.

Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168.810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No: 12169753.6 dated Sep. 14, 2012.
European Search Report for European Application No: 11168458.5 dated Jul. 21, 2011.
U.S. Appl. No. 12/336,970, filed Dec. 17, 2008, Sremcich et al.

\* cited by examiner

APPARATUS FOR PERFORMING AN ELECTROSURGICAL PROCEDURE

BACKGROUND

1. Technical Field

The present disclosure relates to an apparatus for performing an electrosurgical procedure. More particularly, the present disclosure relates to an electrosurgical apparatus including an end effector assembly having a pair of jaw members that provide a mechanical advantage at the end effector.

2. Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Typically, one or more driving mechanisms, e.g., a drive assembly including a drive rod, is utilized to cooperate with one or more components operatively associated with the end effector to impart movement to one or both of the jaw members.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more types of springs, e.g., a compression spring, may operably couple to the handle assembly associated with the electrosurgical forceps. In this instance, the spring is typically operatively associated with the drive assembly to facilitate actuation of a movable handle associated with the handle assembly to ensure that a specific closure force between the jaw members is maintained within one or more suitable working ranges.

In certain instances, the shaft may bend or deform during the course of an electrosurgical procedure. For example, under certain circumstances, a clinician may intentionally bend or articulate the shaft to gain desired mechanical advantage at the surgical site. Or, under certain circumstances, the surgical environment may cause unintentional or unwanted bending or flexing of the shaft, such as, for example, in the instance where the shaft is a component of a catheter-based electrosurgical forceps. More particularly, shafts associated with catheter-based electrosurgical forceps are typically designed to function with relatively small jaw members, e.g., jaw members that are configured to pass through openings that are 3 mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) the frictional losses associated with drive rod translating through the shaft are transferred to the spring in the housing, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument.

An increased mechanical advantage and/or mechanical efficiency with respect to transferring the closure force(s) from the handle assembly to the jaw members may prove advantageous in the relevant art.

SUMMARY

The present disclosure provides an endoscopic forceps. The endoscopic forceps includes a housing having a shaft that extends therefrom and defines a longitudinal axis therethrough. An end effector assembly is operatively connected to a distal end of the shaft and includes a pair of first and second jaw members. The first and second jaw members are pivotably coupled to one another. One of the first and second jaw members is movable relative to the other jaw member from an open position, wherein the first and second jaw members are disposed in spaced relation relative to one another, to a clamping position, wherein the first and second jaw members cooperate to grasp tissue therebetween. A drive mechanism includes a driving structure in operative communication with one or more cam slots operably disposed on one or both of the first and second jaw members. The driving structure includes one or more detents, wherein the distal end of the driving structure is substantially resilient and functions as a cantilever spring that is configured to flex away from the longitudinal axis when the distal tip is positioned at the proximal end of the cam slot and tissue is positioned between the first and second jaw members.

The present disclosure provides a forceps. The forceps includes a housing having a shaft that extends therefrom and defines a longitudinal axis therethrough. An end effector assembly is operatively connected to a distal end of the shaft and includes a pair of first and second jaw members. The first and second jaw members are pivotably coupled to one another. One of the first and second jaw members is movable relative to the other jaw member from a clamping position, wherein the first and second jaw members cooperate to grasp tissue therebetween, to an open position, wherein the first and second jaw members are disposed in spaced relation relative to one another. A drive mechanism includes a drive wire having a substantially resilient distal end including a distal tip with a caroming member in operative communication with one or more cam slots operably disposed on the movable jaw member. The drive wire includes at least one detent. One or more stop members are operably disposed adjacent a distal end of the shaft and are configured such that contact between the stop member and detent corresponds to the distal tip being positioned at a proximal end of the cam slot causing the at least one movable jaw member to move from the clamping position to the open position.

BRIEF DESCRIPTION OF THE DRAWING

Various embodiments of the present disclosure are described hereinbelow with references to the drawings, wherein.

DETAILED DESCRIPTION

Figure 1A:
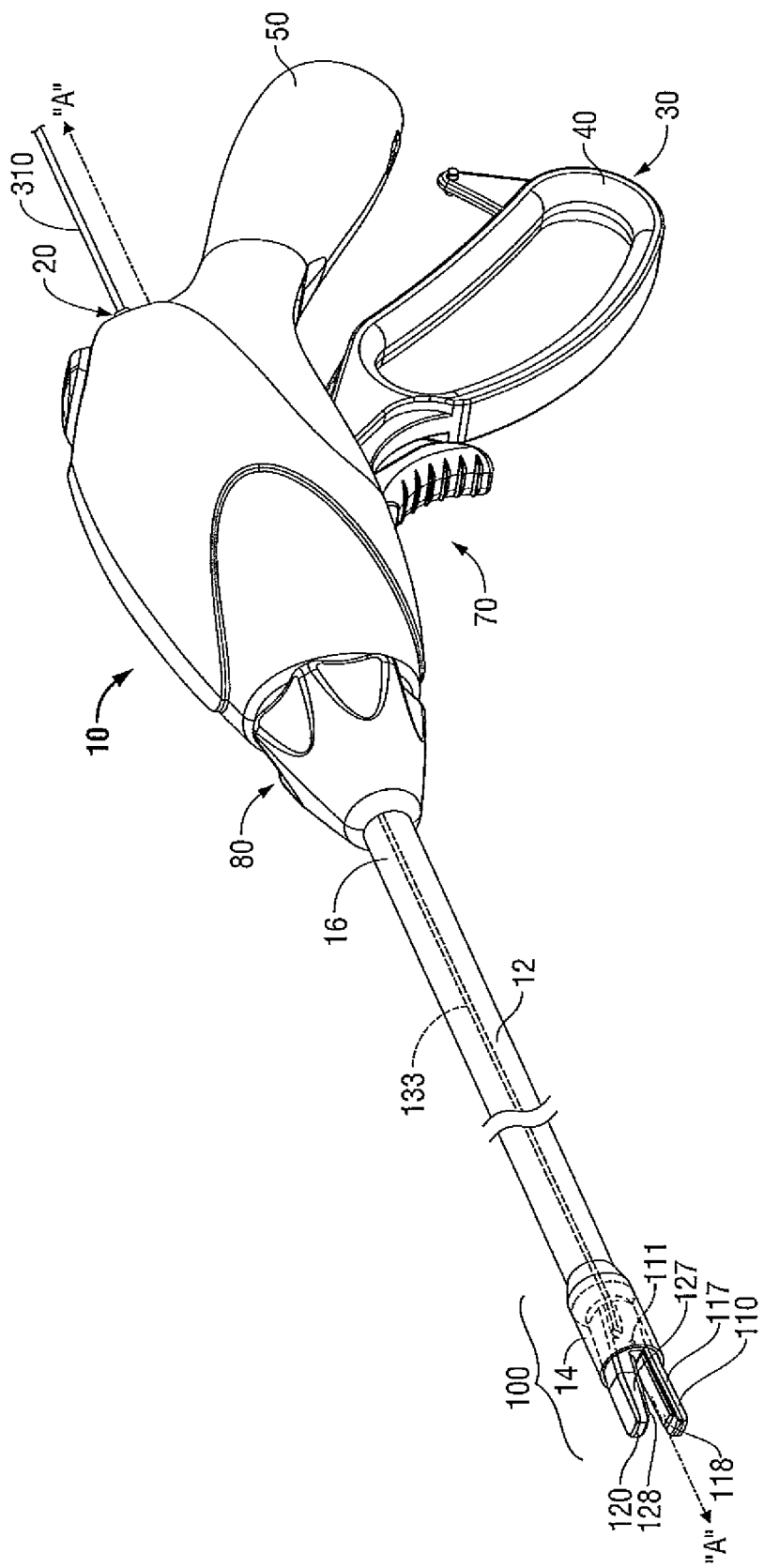
FIG. 1A is a side, perspective view of an endoscopic bipolar forceps showing an end effector assembly including jaw members according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end which is closer to the user, while the term "distal" will refer to an end that is farther from the user.

Figure 1B:
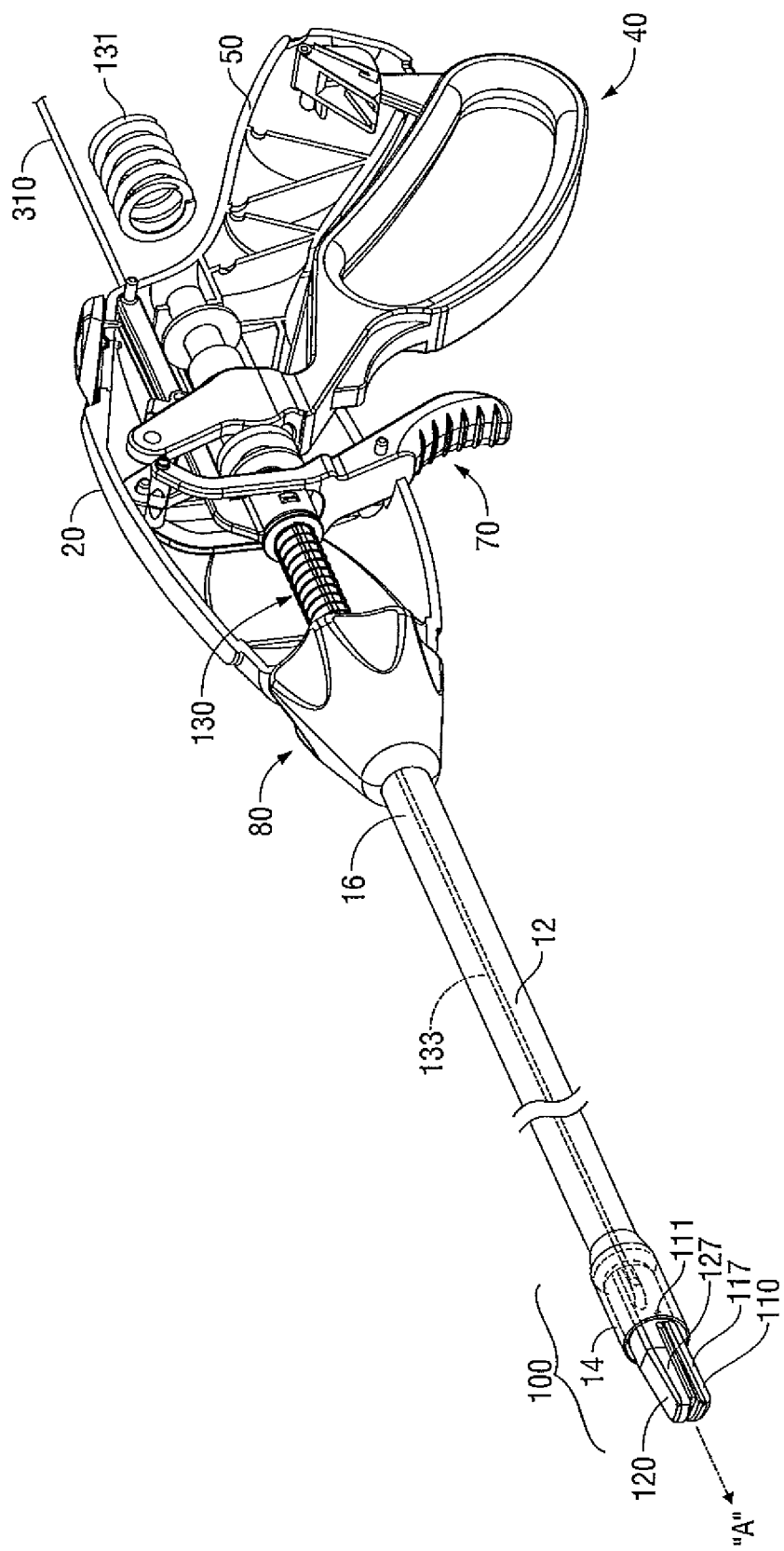
FIG. 1B is a side, perspective view of the endoscopic bipolar forceps depicted in FIG. 1A illustrating internal components associated with a handle assembly associated with the endoscopic bipolar forceps.

With reference to FIGS. 1A and 1B, an illustrative embodiment of an electrosurgical apparatus, e.g., a bipolar forceps 10 (forceps 10) is shown. Forceps 10 is operatively and selectively coupled to an electrosurgical generator (not shown) for performing an electrosurgical procedure. As noted above, an electrosurgical procedure may include sealing, cutting, cauterizing coagulating, desiccating, and fulgurating tissue all of which may employ RF energy. The electrosurgical generator may be configured for monopolar and/or bipolar modes of operation and may include or be in operative communication with a system that may include one or more processors in operative communication with one or more control modules (not shown) that are executable on the processor. The control module may be configured to instruct one or more modules to transmit electrosurgical energy, which may be in the form of a wave or signal/pulse, via one or more cables (e.g., an electrosurgical cable 310) to the forceps 10.

Forceps 10 is shown configured for use with various electrosurgical procedures and generally includes a housing 20, electrosurgical cable 310 that connects the forceps 10 to the electrosurgical generator, a rotating assembly 80 and a trigger assembly 70. For a more detailed description of the rotating assembly 80, trigger assembly 70, and electrosurgical cable 310 (including line-feed configurations and/or connections), reference is made to commonly-owned U.S. patent application Ser. No. 11/595,194 filed on Nov. 9, 2006, now U.S. Patent Publication No. 2007/0173814.

With continued reference to FIGS. 1A and 1B, forceps 10 includes a shaft 12 that has a distal end 14 configured to mechanically engage an end effector assembly 100 operably associated with the forceps 10 and a proximal end 16 that mechanically engages the housing 20.

Figure 2A:
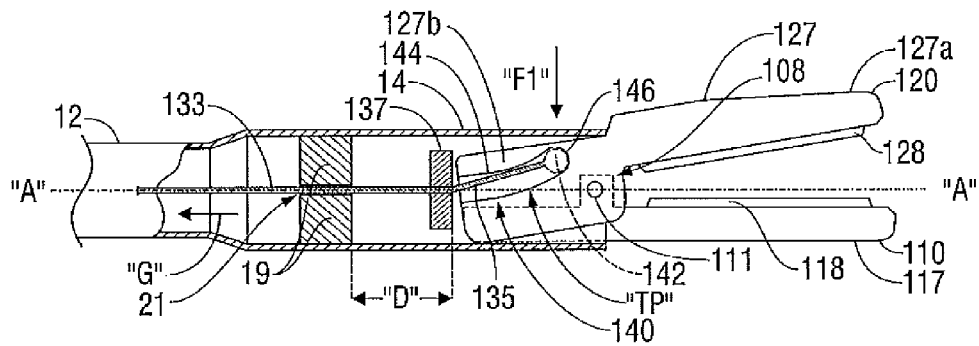
FIGS. 2A-2C are schematic views of the jaw members depicted in FIGS. 1A and 1B illustrating a distal end of a driving structure according to an embodiment of the present disclosure.

One or more positioning structures are operably associated with the shaft 12. More particularly, one or more stop members 19 of suitable proportion are operably disposed adjacent the distal end 14 of the shaft 12 (FIG. 2A). Stop member 19 includes a generally circumferential configuration and is operably coupled to an internal frame of the shaft 12 by one or more suitable coupling methods. In the illustrated embodiment, stop member 19 is monolithically formed with the shaft 12. Stop member 19 is in operative communication with a drive mechanism 130 (FIG. 1B). Specifically, stop member 19 includes an aperture 21 that is dimensioned to receive a driving structure 133 that is operably associated with the drive mechanism 130. More specifically, aperture 21 includes a diameter that accommodates proximal and distal translation of the driving structure 133 therethrough. Stop member 19 is configured to limit and/or prevent proximal translation of the driving structure 133, or operative component associated therewith, described in greater detail below.

Handle assembly 30 includes a fixed handle 50 and movable handle 40 (FIGS. 1A and 1B). In one particular embodiment, fixed handle 50 is integrally associated with housing 20. Movable handle 40 is movable relative to fixed handle 50 for effecting movement of one or more components, e.g., driving structure 133, operably associated with drive mechanism 130 (FIG. 1B).

Drive mechanism 130 is in operative communication with movable handle 40 (see FIGS. 1A and 1B) for imparting movement of one or, in some instances, both of a pair of jaw members 110, 120 of end effector assembly 100. More particularly, one or more suitable mechanical interfaces, e.g., a linkage interface, gear interface, or combination thereof operably couples the movable handle 40 to the drive mechanism 130. In the embodiment illustrated in FIGS. 1A and 1B, proximal movement of the movable handle 40 moves the moveable jaw member, e.g., jaw member 120, from the normally open position to the clamping position.

Conventional drive mechanisms and/or assemblies typically utilize one or more types of springs, e.g., a compression spring, to facilitate closing the jaw members 110 and 120. For illustrative purposes, a compression spring 131 (see FIG. 1B) is shown separated from the housing 20. In accordance with the present disclosure, the combination of the drive mechanism 130 including driving structure 133 that operably couples to a cam slot 140 (FIGS. 2A-2C) operably associated with one or both of the jaw members 110 and 120 functions to facilitate moving the jaw members 110 and 120 and, thus, may eliminate the need for the compression spring 131.

Driving structure 133 is configured such that proximal movement thereof causes jaw member 120 to move from the open position (FIGS. 1A and 2A) to the closed or clamping position (FIGS. 1B and 2B) and vice versa. To this end, driving structure 133 may be any suitable driving mechanism including but not limited to a wire, rod, cable, band, etc. In the illustrated embodiment, driving structure 133 is a drive wire of suitable proportion that is dimensioned to translate within the aperture 21 of the stop member 19 (see FIG. 2A, for example). Drive wire 133 is dimensioned such that the drive wire 133 does not to "buckle" or "kink" when the drive wire 133 is moved proximally and/or distally within the shaft 12 and through the aperture 21.

Drive wire 133 includes a proximal end (not explicitly shown) that is in operative communication with the movable handle 40.

Figure 2B:
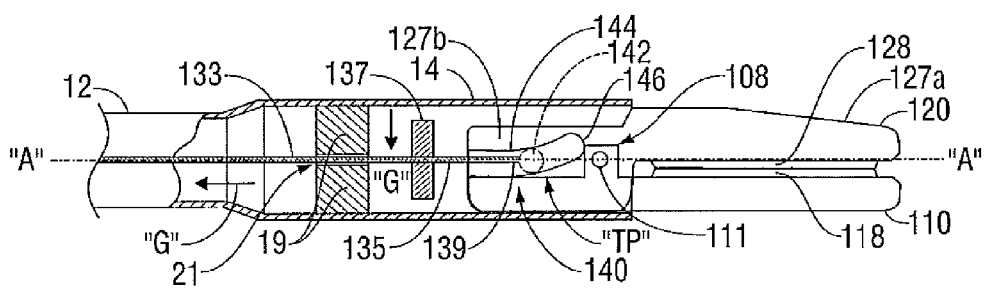
Figure 2C:
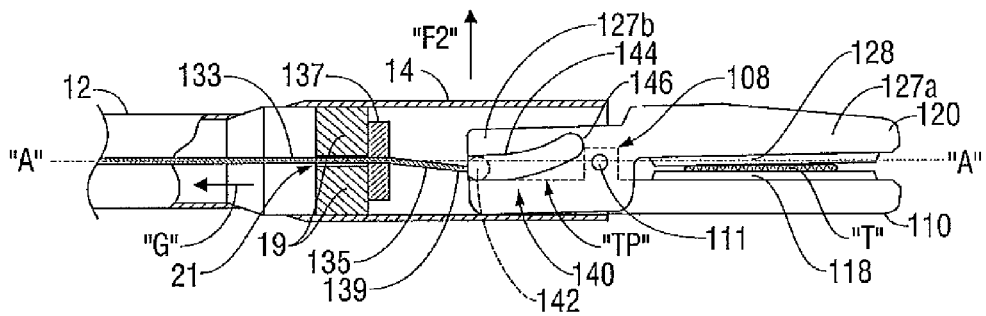

A blocking member in the form of a detent 137 having dimensions of suitable proportion is operably associated with the drive wire 133 (FIGS. 2A-2C). In the illustrated embodiment, detent 137 includes a generally cylindrical configuration and is operably coupled to the drive wire 133 by one or more suitable coupling methods. For illustrative purposes, detent 137 is shown monolithically formed with the drive wire 133. Detent 137 is disposed adjacent a distal end 135 of the drive wire 133 and distally relative to the stop member 19 (FIGS. 2A-2C).

Detent 137 is configured to contact stop member 19 when the movable handle 40 is moved proximally and the drive wire 133 is moved proximally through the stop member 19. Contact between the stop member 19 and detent 137 limits and/or prevents movement or translation of the drive wire 133 through the stop member 19 thereby limiting movement of distal end 135 within the cam slot 140 such that a portion, e.g., a distal tip 139, of the distal end 135 is positioned at a predetermined location, e.g., a proximal end 144, of the cam slot 140. That is drive wire 133 and, thus, distal end 135 are configured to move a distance "D" that is approximately equal to the distance that the distal tip 139 moves within the cam slot 140 when the movable handle 40 is moved proximally, see FIG. 2A. Moving and/or positioning the distal tip 139 the predetermined distance "D" within the cam slot 140 provides a required closure force between the jaw members 110 and 120 when tissue is positioned between the jaw members 110 and 120, described in greater detail below.

Distal end 135 includes a substantially linear or straight configuration that is in general alignment with the cam slot 140 when the first and second jaw members 110 and 120 are in a "neutral" condition. As used herein, the "neutral" condition refers to the condition where the distal tip 139 is positioned at the proximal end 144 and without tissue positioned the jaw members 110 and 120 (FIG. 2B). Distal end 135 functions as a cantilever spring or "spring-board" that is configured to "flex" away from the longitudinal axis "A-A" when the distal tip 139 is positioned at the proximal end 144 of the cam slot 140 and tissue is positioned between the jaw members 110 and 120 (FIG. 2C). When the distal end 135 is in the "flexed" position illustrated in FIG. 2C, the distal end 135 exerts an upward force "F2" that is directed toward the longitudinal axis "A-A." Likewise, when the distal tip 139 is positioned at the distal end 146 of the cam slot 140, the distal end 135 is configured to "flex" away from the longitudinal axis "A-A." However, when the distal end 135 is in the "flexed" position illustrated in FIG. 2A, the distal end 135 exerts a downward force "F1" that is directed toward the longitudinal axis "A-A." The downward force "F1" maintains the jaw member 120 in a spaced-apart relation with respect to the jaw member 110. That is, the downward force "F1" pivots the jaw member 120 away from the jaw member 110 and into the open position. This downward force "F1" is a result of the configuration of the cam slot 140 and the size and/or length of the distal end 135.

Distal end 135, or portion thereof, e.g., distal tip 139, is configured to translate or move within one or, in some instances, both of the jaw members 110 and 120. For illustrative purposes, the end effector 100 is shown having a unilateral jaw design, i.e., jaw member 120 is configured to pivot and/or rotate with respect to jaw member 110. Accordingly, distal end 135 is configured to translate or move within jaw member 120. More particularly, the distal tip 139 of the distal end 135 is in operative communication with the cam slot 140 and is configured to translate or move within the cam slot 140 and move the jaw member 120 from the open to the closed or clamping positions and vice versa. In the clamping position, and with tissue positioned between the jaw members 110 and 120, the distal end 135 generates a closure force ranging from about 3 kg/cm² to about 16 kg/cm² between the jaw members 110 and 120.

In certain embodiments, a camming member 142 (shown in phantom) may be operably coupled to the distal tip 139, via one or more suitable coupling methods, e.g., via a spot weld. Camming member 142 is configured to facilitate moving (and in certain instances camming the jaw member 120) the distal tip 139 and/or distal end 135 within the cam slot, i.e., past a transition point "Tp" of the cam slot 140, see FIG. 2A. The transition point "Tp" corresponds to location in the cam slot 140 that is in substantial alignment with a pivot pin 111, see FIG. 2A, for example.

End effector assembly 100 is illustrated operably disposed at the distal end 14 of the shaft 12 (FIGS. 1A and 1B). End effector assembly 100 includes opposing jaw members 110 and 120 that mutually cooperate to grasp, seal and, in some cases, divide large tubular vessels and large vascular tissues.

As noted above, in the illustrated embodiment, jaw member 110 is stationary and the jaw member 120 is movable relative to the jaw member 110. Jaw members 110, 120 are operatively and pivotably coupled to each other and located adjacent the distal end 14 of shaft 12. Respective electrically conductive seal plates 118 and 128 are operably supported on and secured to respective jaw housings 117 and 127 of respective the jaw members 110 and 120. Jaw members 110 and 120 including respective jaw housings 117 and 127, and operative components associated therewith, may be formed from any suitable material, including but not limited to metal, metal alloys, plastic, plastic composites, and so forth.

Jaw housing 127 and 117 of the respective jaw members 110 and 120 are substantially identical to each other. In view thereof, the operative features of jaw housing 127 are described in detail, and only those features that are unique to jaw member 110 are described hereinafter.

With reference to FIGS. 2A-2C, an embodiment of jaw housing 127 is illustrated. Jaw housing 127 includes a distal end 127a that is configured to operably support seal plate 128 and a proximal end 127b that operably couples to the distal end 14 of shaft 12. Proximal end 127b includes a generally rectangular configuration, FIG. 2A, and is dimensioned to move, e.g., pivot, within the shaft 12 from the closed or clamping position to the open position. Proximal end 127b is dimensioned to include one or more cam slots 140. A pivot pin 111 couples the first and second jaw members 110 and 120, respectively (FIG. 2A) for pivotal movement relative to one another.

Cam slot 140 includes a generally straight, elongated configuration having proximal end 144 that is substantially aligned with the longitudinal axis "A-A." Proximal end 144 of the cam slot 140 is configured such that with tissue positioned between the jaw members 110 and 120, and when the detent 137 contacts the stop member 19, the distal tip 139 of the distal end 135 is positioned about the proximal end 144. With the distal tip 139 positioned about the proximal end 144, distal end 135 pivots away, e.g., downward, from the longitudinal axis "A-A" and exerts an upward force "F2" such that the jaw member 120 clamps down on tissue with a closure force ranging from about 3 kg/cm² to about 16 kg/cm².

Cam slot 140 extends substantially along a length of the proximal end 127b and includes a distal end 146 that is elevated or "offset" with respect to the proximal end 144. More particularly, distal end 146 is disposed at a predetermined position above the pivot pin 111 (FIG. 2A). Positioning the distal end 146 above the pivot pin 111 facilitates maintaining the jaw member 120 in the open configuration. That is, with the distal tip 139 positioned about the distal end 146, the distal end 135 pivots away, e.g., upward, from the longitudinal axis "A-A" and exerts a downward force "F1" such that the jaw member 120 moves away from the jaw member 110.

Unlike jaw housing 127 of jaw member 120, jaw housing 117 of jaw member 110 does not include a cam slot 140, i.e., due to the unilateral jaw configuration, and does not move with respect to the jaw member 120.

The jaw members 110 and 120 may be coupled to each other via any suitable coupling methods. In the illustrated embodiment, an opening 108 is defined in and extends through the each of the jaw housing 117 and 127 and is configured to receive pivot pin 111. Opening 108 is shown engaged with pivot pin 111 and as such is not explicitly visible.

In an assembled configuration, pivot pin 111 is positioned within the openings associated with each of the jaw members 110 and 120. Once assembled, the jaw members 120 and/or jaw member 110 may be pivotally supported at the distal end 14 of the shaft 12 by known methods, such as, for example, by the method described in commonly-owned U.S. Pat. No. 7,597,693 to Garrison filed on Jun. 13, 2003.

In use, initially distal tip 139 of the distal end 135 is positioned at distal end 146 of the cam slot 140 and the jaw members 110 and 120 are in an open configuration (see FIG. 1A in combination with FIG. 2A). Subsequently, tissue is positioned between the jaw members 110 and 120. Movable handle 40 is moved proximally (FIG. 1B), which, in turn, causes the drive wire 133 including detent 137 to move proximally in the direction indicated by directional arrow "G" (FIG. 2A). When detent 137 and distal end 135 including distal tip 139 have moved the predetermined distance "D," the detent 137 contacts the stop member 19 and the distal tip 139 is positioned at the proximal end 144 of the cam slot 140. In this position, the distal end 135 and/or distal tip 139 provides the upward force "F2" such that the jaw member 120 clamps down on tissue positioned between the jaw members 110 and 120 (see FIG. 1B in combination with FIG. 2C) with a closure force that ranges from about 3 kg/cm$^2$ to about 16 kg/cm$^2$. Subsequently, electrosurgical energy is transmitted to the seal plates 118 and 128 such that an electrosurgical effect, e.g., tissue seal, is achieved at tissue. Thereafter, movable handle 40 is released, which, in turn, causes distal tip 139 of the drive wire 133 to return to the distal end 146 of the cam slot 140 and the jaw member 120 to move back to open position. The drive mechanism 130 including a distal end 135 configured as a cantilever spring and the cam slot 140 associated with the jaw member 120 provides an additional mechanical advantage at the jaws 110 and 120 and helps reduce the frictional losses that are typically associated with conventional forceps when a drive rod is translated within a shaft to make the necessary closure force to seal tissue, i.e., the closure force is offloaded and/or diminished by the distal end 135 of the drive wire 133 and cam slot configuration 140.

From the foregoing and with reference to the various figure drawings, those skilled in the art will appreciate that certain modifications can also be made to the present disclosure without departing from the scope of the same. For example, in certain instances it may prove useful to have both of the jaw members 110 and 120 move relative to each other. In this instance, a cam slot 140 may be operably disposed on each of the jaw members 110 and 120. Accordingly, a drive mechanism 130 may include a pair of drive wires 133 that operably couple to a respective jaw member.

It is contemplated that in certain instances one or more resilient members, e.g., compression spring (not shown), may be operably associated with or coupled to either the stop member 19 or detent 137. In this instance, the spring may be configured to provide a "pushing" force against the proximal surface of the detent 137. This "pushing" force is configured to facilitate "bending" or "flexing" of the distal end 135.

It is contemplated that in certain embodiments, the stop 19 and detent 137 may function as or include a ratchet and pawl system. In this instance, the stop 19 and detent 137 may be configured to lock the jaw members 110 and 120 in one or more positions, e.g., the clamping position.

It is contemplated that in some embodiments, a distal end that is configured to rotate within a cam slot that is operably disposed on the jaw member 120 may be utilized with the drive mechanism 130 to impart movement of the jaw member 120.

Figure 3A:
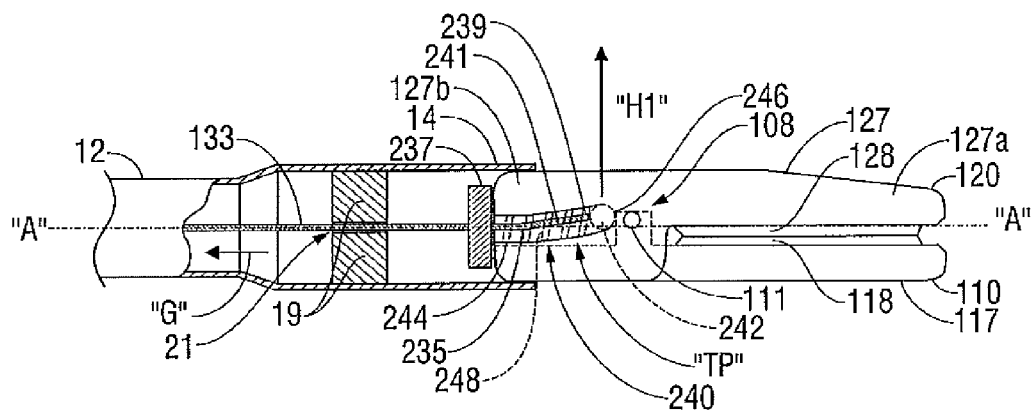
FIGS. 3A and 3B are schematic views of the jaw members depicted in FIGS. 1A and 1B illustrating a distal end of a driving structure according to another embodiment of the present disclosure.
Figure 3B:
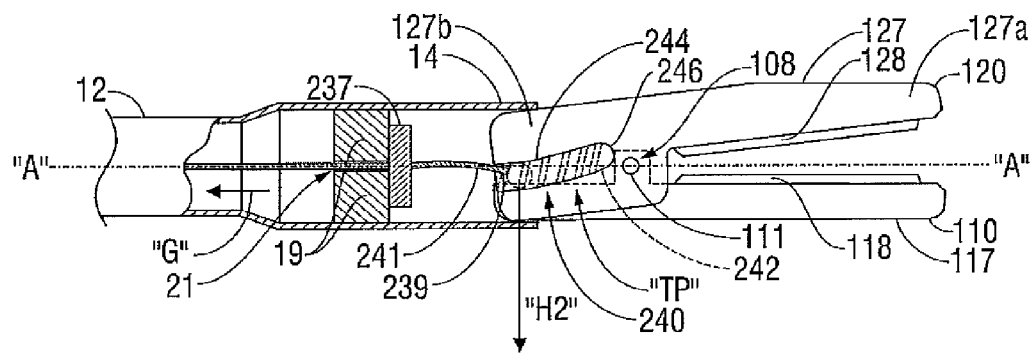

More particularly, and with reference to FIGS. 3A and 3B, a rotatable distal end 235 is illustrated. Distal end 235 is configured to rotate within a cam slot 240 when the drive wire 133 is moved, e.g., proximally or distally, see FIGS. 3A and 3B. More particularly, the distal end 235 is rotatable within the cam slot 240 during translation therein when the movable handle 40 is moved proximally and/or distally. To this end, the distal end 235 is rotatably coupled to the drive wire 133 by one or more suitable coupling methods. In the embodiment illustrated in FIGS. 3A and 3B, the distal end 235 is coupled to a detent 237 of the drive wire 133 via a threaded screw connection, not explicitly shown. For example, the distal end 235 may include a threaded male end that is configured to screw into a threaded female end on the detent 237. In this instance, when the drive wire 133 is moved, e.g., either proximally or distally, the distal end 235 will rotate within the cam slot 240 and with respect to the detent 237, i.e. the distal end 235 screws into or out of the detent 237.

Distal end 235 includes a generally arcuate portion 241 that facilitates maintaining the jaw member 120 in the open or clamped configuration. More particularly, the arcuate portion 241 provides an upward force "H1" that is directed away from the longitudinal axis "A-A," when the distal tip 239 is positioned about a distal end 246 of the cam slot 240 (FIG. 3A). Likewise, the arcuate portion 241 provides a downward force "H2" that is directed away from the longitudinal axis "A-A," when the distal tip 239 is positioned about a proximal end 244 of the cam slot 240 (FIG. 3B). The distal end 235 rotates from an initial position that corresponds to the jaw member 120 in the clamping position, see FIG. 3A, to a subsequent or final position, that corresponds to the jaw member 120 in the open position, see FIG. 3B.

A significant difference of a drive mechanism 130 that utilizes the distal end 235 when compared with a drive mechanism 130 that utilizes the distal end 135 is that, because the distal end 235 of the drive wire 233 rotates within the cam slot 240, machining tolerances that may be associated with the manufacture of the cam slot 240 are minimized. More particularly, unlike the distal end 146, the distal end 246 of the cam slot 240 may be positioned above, below or aligned with the pivot pin 111. That is, the upward force "H1" generated by the arcuate portion 241 of the distal end 235 facilitates maintaining the movable jaw member 120 in the clamping configuration when the distal tip 239 is positioned at the distal end 246 of the cam slot 240. For illustrative purposes, the distal end 246 is shown disposed substantially aligned with the pivot pin 111.

Cam slot 240 includes one or more tracks, bores, grooves, protuberances, detents, etc. that are configured to guide, direct, turn, maneuver, or otherwise rotate the distal tip 239 when the distal end 235 is moved within and along a length of the cam slot 240. For example, and in one particular embodiment, a generally helical groove or bore 248 is disposed within the cam slot 240 and extends along a length thereof. The helical bore 248 may be dimensioned to receive a detent or protuberance, e.g., a camming member 242 that is configured to move therein when the distal end 235 is moved. More particularly, when the distal end 235 including the distal tip 239 moves within the cam slot 240, the caroming member 242 moves within the helical bore 248. A path or course as defined by the helical bore 248 is of such configuration that when the camming member 242 travels along a predetermined length thereof, the distal end 235 is caused to rotate from the initial position to the final position. Other methods of rotating the distal end 235 within the cam slot 240 are contemplated and appreciated.

In use, initially distal tip 239 of the distal end 235 is positioned at distal end 246 of the cam slot 240 and the jaw members 110 and 120 are in a closed configuration (FIG. 3A). Movable handle 40 is moved proximally, which, in turn, causes the drive wire 133 including detent 237 to move proximally in the direction indicated by directional arrow "G"

(FIG. 3B). As the distal end 235 moves proximally, the distal tip 239 moves within and follows the path, e.g., the generally helical path, of the helical bore 248 disposed within the cam slot 240, which, in turn, causes the distal end 235 including the arcuate portion 241 to rotate, e.g., in a counter-clockwise direction, and "unscrew" from the detent 237. When the detent 237 and distal end 235 including distal tip 239 have moved a predetermined distance "D," detent 237 contacts the stop member 19 and the distal tip 239 is positioned at the proximal end 244 of the cam slot 240. In this position, the arcuate portion 241 of the distal end 235 and/or distal tip 239 provides a downward force "H2" such that the jaw member 120 moves away from jaw member 110 and toward the open position (FIG. 3B). Tissue is positioned between the jaw members 110 and 120. Thereafter, movable handle 40 is released, which, in turn, causes distal tip 239 of the drive wire 133 to return to the distal end 246 of the cam slot 240 and the jaw member 120 to move back to the closed or clamped position such that tissue is grasped therebetween. Subsequently, electrosurgical energy is transmitted to the seal plates 118 and 128 such that an electrosurgical effect, e.g., tissue seal, is achieved at tissue. The drive mechanism 130 including a rotatable distal end 235 that is configured to translate and rotate within the cam slot 240 associated with the jaw member 120 provides the same mechanical advantage as described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic forceps, comprising:
   a housing having a shaft that extends therefrom and defines a longitudinal axis therethrough;
   an end effector assembly operatively connected to a distal end of the shaft and including a pair of first and second jaw members pivotably coupled to one another, at least one of the first and second jaw members movable relative to the other jaw member from an open position, wherein the first and second jaw members are disposed in spaced relation relative to one another, to a clamping position, wherein the first and second jaw members cooperate to grasp tissue therebetween; and
   a drive mechanism including a driving structure having at least one detent supported thereon, the driving structure including a distal end with a distal tip in operative communication with at least one cam slot operably defined within the at least one movable jaw member, the distal end disposed distally relative to the at least one detent and proximally relative to the distal tip,
   wherein the distal end of the driving structure is substantially resilient and functions as a cantilever spring that is configured to flex away from the longitudinal axis when the distal tip is positioned at a proximal end of the cam slot and tissue is positioned between the first and second jaw members,
   wherein the at least one cam slot includes a generally straight configuration having a proximal end substantially aligned with a pivot pin that pivotably couples the first and second jaw members, and a distal end offset from the proximal end and above the pivot pin.

2. An endoscopic forceps according to claim 1, wherein a distal end of at least one stop member disposed adjacent the distal end of the shaft contacts a proximal end of the at least one detent when the driving structure is moved proximally.

3. An endoscopic forceps according to claim 1, wherein a camming structure is operably coupled to the distal tip of the driving structure and operably disposed within the at least one cam slot.

4. An endoscopic forceps according to claim 1, wherein at least one stop member is operably disposed adjacent a distal end of the shaft and configured to contact the at least one detent when the driving structure is moved proximally such that contact between the at least one stop member and the at least one detent corresponds to the distal tip being positioned at a proximal end of the cam slot causing the at least one movable jaw member to move from the open position to the clamping position.

5. An endoscopic forceps according to claim 4, wherein when the distal tip of the driving structure is disposed at the proximal end of the cam slot and tissue is positioned between the first and second jaw members, a closure force ranging from about 3 kg/cm$^2$ to about 16 kg/cm$^2$ is present between the first and second jaw members.

6. An endoscopic forceps according to claim 1, wherein the driving structure is selected from the group consisting of a wire, rod, cable and band.

7. An endoscopic forceps according to claim 1, further comprising a movable handle that is operably associated with the endoscopic forceps and configured to actuate the driving mechanism when the movable handle is moved proximally such that the at least one movable jaw member moves from the open position to the clamping position.

8. A forceps, comprising:
   a housing having a shaft that extends therefrom and defines a longitudinal axis therethrough;
   an end effector assembly operatively connected to a distal end of the shaft and including a movable jaw member and a stationary jaw member pivotably coupled to one another, the movable jaw member movable relative to the stationary jaw member from a clamping position, wherein the movable and stationary jaw members cooperate to grasp tissue therebetween, to an open position, wherein the movable and stationary jaw members are disposed in spaced relation relative to one another;
   a drive mechanism including a drive wire having a substantially resilient distal end including a distal tip with a camming member in operative communication with at least one cam slot operably disposed on the movable jaw member, the drive wire including at least one detent; and
   at least one stop member operably disposed adjacent a distal end of the shaft and configured to contact the at least one detent when the driving structure is moved proximally such that contact between the at least one stop member and the at least one detent corresponds to the distal tip being positioned at a proximal end of the cam slot causing the at least one movable jaw member to move from the clamping position to the open position.

9. A forceps according to claim 8, wherein the distal end of the driving structure is rotatably coupled to the detent.

10. A forceps according to claim 8, wherein the cam slot includes a helical bore extending along a length thereof, the helical bore configured to receive the distal tip of the distal end therein such that the distal end including the distal tip is rotatable within the cam slot from an initial position wherein the first and second jaw members are in the clamping position to a subsequent position wherein the first and second jaw members are in the open position.

11. A forceps according to claim 8, wherein the distal end of the driving structure includes a threaded male end that is configured to screw into a female threaded end of the detent.

12. A forceps according to claim 8, wherein when the distal tip of the driving structure is disposed at the distal end of the cam slot, a closure force ranging from about 3 kg/cm$^2$ to about 16 kg/cm$^2$ is present between the first and second jaw members.

13. A forceps according to claim 8, wherein the driving structure is selected from the group consisting of a wire, rod, cable and band.

14. A forceps according to claim 8, further comprising a movable handle that is operably associated with the endoscopic forceps and configured to actuate the driving mechanism when the movable handle is moved proximally such that the at least one movable jaw member moves from the open position to the clamping position.

15. A forceps, comprising:
- a housing having a shaft that extends therefrom and defines a longitudinal axis therethrough;
- an end effector assembly operatively connected to a distal end of the shaft and including a pair of first and second jaw members pivotably coupled to one another, at least one of the first and second jaw members movable relative to the other jaw member from an open position, wherein the first and second jaw members are disposed in spaced relation relative to one another, to a clamping position, wherein the first and second jaw members cooperate to grasp tissue therebetween; and
- a drive mechanism including a driving structure having at least one detent supported thereon, the driving structure including a distal end with a distal tip in operative communication with and translatable along the longitudinal axis within at least one cam slot operably defined within the at least one movable jaw member, the distal end disposed distally relative to the at least one detent and proximally relative to the distal tip,
- wherein the distal end of the driving structure is substantially resilient and functions as a cantilever spring that is configured to flex away from the longitudinal axis when the distal tip is positioned at the proximal end of the cam slot and tissue is positioned between the first and second jaw members.

* * * * *